United States Patent
Tass

(10) Patent No.: US 9,826,916 B2
(45) Date of Patent: Nov. 28, 2017

(54) DEVICE AND METHOD FOR EXAMINING A PHASE DISTRIBUTION USED TO DETERMINE A PATHOLOGICAL INTERACTION BETWEEN DIFFERENT AREAS OF THE BRAIN

(71) Applicant: FORSCHUNGSZENTRUM JÜLICH GMBH, Jülich (DE)

(72) Inventor: Peter Alexander Tass, Juelich (DE)

(73) Assignee: FORSCHUNGSZENTRUM JÜLICH GMBH, Jülich (DE)

(*) Notice: Subject to any disclaimer, the term of this patent is extended or adjusted under 35 U.S.C. 154(b) by 251 days.

(21) Appl. No.: 14/432,909

(22) PCT Filed: Oct. 2, 2013

(86) PCT No.: PCT/EP2013/002971
§ 371 (c)(1),
(2) Date: Apr. 1, 2015

(87) PCT Pub. No.: WO2014/053244
PCT Pub. Date: Apr. 10, 2014

(65) Prior Publication Data
US 2015/0238104 A1     Aug. 27, 2015

(30) Foreign Application Priority Data
Oct. 2, 2012   (DE) .................. 10 2012 218 057

(51) Int. Cl.
*A61B 5/04*     (2006.01)
*A61B 5/00*     (2006.01)
(Continued)

(52) U.S. Cl.
CPC ...... *A61B 5/04014* (2013.01); *A61B 5/04009* (2013.01); *A61B 5/0478* (2013.01);
(Continued)

(58) Field of Classification Search
CPC ............ A61B 5/04014; A61B 5/04847; A61B 5/04009; A61B 5/7246; A61B 5/0478;
(Continued)

(56) References Cited

U.S. PATENT DOCUMENTS 6,658,287 B1 * 12/2003 Litt ...................... A61B 5/0476
600/544
6,845,342 B1   1/2005 Basser et al.
(Continued)

FOREIGN PATENT DOCUMENTS

CN      1774279 A    5/2006
CN    101801455 A    8/2010
(Continued)

OTHER PUBLICATIONS

"Lehrbuch der Anatomie des Menschen" Textbook of Human Anatomy, Presented with Emphasis on Functional Relationships, 3rd. vol., Nervous System, Skin and Sensory Organs, Urban and Schwarzenberg, Munich 1964.
(Continued)

*Primary Examiner* — Sanjay Cattungal
(74) *Attorney, Agent, or Firm* — Arent Fox LLP

(57) ABSTRACT

A device for examining a pathological interaction between different brain areas, including a stimulation unit, which administers identical stimuli to a patient in a sequential manner, wherein the stimuli stimulate neurons of the patient in the brain areas to be examined, a measuring unit for recording measurement signals that represent a neural activity of the stimulated neurons, and a control and analysis unit for controlling the stimulation unit and for analyzing the measurement signals. The control and analysis unit transforms the measurement signals into the complex plane, examines the distribution of the phases of stimuli of the measurement signals absorbed by the measuring unit in
(Continued)

response to the stimuli delivered to the patient, and determines the probability, with which the phase distribution differs from a uniform distribution, in order to ascertain whether a pathological interaction between the brain areas exists.

22 Claims, 3 Drawing Sheets

(51) Int. Cl.
*A61N 1/36* (2006.01)
*A61B 5/0484* (2006.01)
*A61B 5/0488* (2006.01)
*A61B 5/0478* (2006.01)
*A61N 1/05* (2006.01)

(52) U.S. Cl.
CPC ........ *A61B 5/0488* (2013.01); *A61B 5/04842* (2013.01); *A61B 5/04845* (2013.01); *A61B 5/04847* (2013.01); *A61B 5/4064* (2013.01); *A61B 5/4082* (2013.01); *A61B 5/4094* (2013.01); *A61B 5/7246* (2013.01); *A61N 1/05* (2013.01); *A61N 1/3605* (2013.01); *A61N 1/36025* (2013.01); *A61B 2562/0214* (2013.01)

(58) Field of Classification Search
CPC .............. A61B 5/04842; A61B 5/0488; A61B 5/04845; A61B 5/4094; A61B 5/4082; A61B 5/4064; A61B 2562/0214; A61N 1/05; A61N 1/36025; A61N 1/3605
USPC ....................................... 600/407–480; 607/3
See application file for complete search history.

(56) References Cited

U.S. PATENT DOCUMENTS

| | | | |
|---|---|---|---|
| 2005/0273017 A1 | 12/2005 | Gordon | |
| 2006/0047324 A1* | 3/2006 | Tass ..................... | A61B 5/0482 607/45 |
| 2007/0161919 A1* | 7/2007 | DiLorenzo ......... | A61B 5/04001 600/544 |
| 2009/0054800 A1 | 2/2009 | Martinerie et al. | |
| 2011/0009921 A1* | 1/2011 | Tass ....................... | A61B 5/486 607/45 |
| 2011/0201977 A1* | 8/2011 | Tass ....................... | A61H 7/004 601/15 |
| 2012/0078323 A1 | 3/2012 | Osorio | |
| 2012/0215114 A1 | 8/2012 | Gratton et al. | |
| 2012/0232862 A1 | 9/2012 | Geerts et al. | |

FOREIGN PATENT DOCUMENTS

| | | |
|---|---|---|
| CN | 102361588 A | 2/2012 |
| DE | 10 2010 016 461 A1 | 10/2011 |
| WO | WO 2004016165 A1 | 2/2004 |
| WO | WO 2010043413 A1 | 4/2010 |

OTHER PUBLICATIONS

Afia F. Mirza et al; "Is There a Relationship between Throbbing Pain and Arterial Pulsations?"; The Journal of Neuroscience, vol. 33, No. 22, May 30, 2012, pp. 7572-7576.
Brian A. Wandell et al; Visual Field Maps in Human Cortex; Neuron 56, Oct. 25, 2007, pp. 366-383.
Constance Hammond et al.; "Pathological synchronization in Parkinson's disease: networks, models and treatments"; TRENDS in Neurosciences, vol. 30, No. 7, 2007, pp. 357-364.
Dave R.M. Langers et al; "Representation of lateralization and tonotopy in primary versus secondary human auditory cortex"; NeuroImage 34, 2007, pp. 264-273.
Deniz Bilecen et al.; "Tonotopic organization of the human auditory cortex as detected by BOLD-FMRI"; Hearing Research 126, 1998, pp. 19-27.
Edward Batschelet, "Circular Statistics in Biology"; Academic Press, London, 1981, pp. 76-79.
G.D. Dawson, M.B., M.Sc.; "A Summatiion Technique for the Detection of Small Evoked Potentials"; Electroencephalogr. Clin. Neurophysiol. 44, 1954, pp. 65-84.
Joshua J. Schulman et al.; "Imaging of thalamocortical dysrhythmia in neuropsychiatry"; Frontiers in Human Neuroscience, vol. 5, Article 69, Jul. 2011, pp. 1-11.
Matti Hamalainen et al.; "Magnetoencephalography—theory, instrumentation, and applications to noninvasive studies of the working human brain"; Reviews of Modern Physics. vol. 65, No. 2, Apr. 1993, pp. 413-497.
N.E. Huang et al.; "The empirical mode decomposition and the Hilbert spectrum for nonlinear and non-stationary time series analysis"; Proc. R. Soc. A: Math. Phys. Eng. Sci. vol. 454, 1998, pp. 903-995.
Nathan Weisz et al.; "Tinnitus Perception and Distress is Related to Abnormal Spontaneous Brain Activity as Measured by Magnetoencephalography"; PLoS Medicine, vol. 2, Issue 6, Jun. 2005, pp. 546-553.
Nicolaas H. Kuiper; "Tests Concerning Random Points on a Circle"; Proceedings of the Koninklijke Nederlandse Akademis van Wetenschappen, Series A 63, 1960, pp. 38-47.
Wei Huang et al.; "Engineering analysis of biological variables: An example of blood pressure over 1 day"; Proc. Natl. Acad. Sci. USA, vol. 95, Apr. 1998, pp. 4816-4821.
Werner Muehinickel et al; "Reorganization of auditory cortex in tinnitus"; Proc. Natl. Acad. Sci. USA, vol 95, Aug. 1998, pp. 10340-10343.
Winfried Schlee et al.; "Mapping cortical hubs in tinnitus"; BMC Biology 80, vol. 7, 2009, pp. 1-14.

* cited by examiner

DEVICE AND METHOD FOR EXAMINING A PHASE DISTRIBUTION USED TO DETERMINE A PATHOLOGICAL INTERACTION BETWEEN DIFFERENT AREAS OF THE BRAIN

CROSS-REFERENCE TO RELATED APPLICATIONS

This application is the U.S. National Stage of International Application No. PCT/EP2013/002971, filed Oct. 2, 2013 and claims the benefit thereof. The International Application claims the benefits of German application No. 10 2012 218 057.5 DE filed Oct. 2, 2012, both of the applications are incorporated by reference herein in their entirety.

FIELD OF TECHNOLOGY

The present invention relates to an apparatus and to a method for examining a pathological interaction between different brain areas.

BACKGROUND

A plurality of neurological and psychiatric diseases are characterized by pathologically increased synchronization of neural populations (cf. e.g. "Pathological synchronization in Parkinson's disease: networks, models and treatments." by C. Hammond, H. Bergman and P. Brown, published in Trends Neurosci. 30, 2007, pages 357 to 364; "Tinnitus Perception and Distress is Related to Abnormal Spontaneous Brain Activity as Measured by Magnetoencephalography" by N. Weisz, S. Moratti, M. Meinzer, K. Dohrmann and T. Elbert, published in PLoS Med 2(6), 2005, pages 546 to 553; "Imaging of Thalamocortical Dysrhythmia in Neuropsychiatry" by J. J. Schulman, R. Cancro, S. Lowe, F. Lu, K. D. Walton and R. R. Llinás, published in Front. Hum. Neurosci, 5, 201.1, page 69). In this case, a large number of neurons synchronously form action potentials, i.e. the participating neurons fire excessively synchronously. In a healthy person, in contrast, the neurons fire with a different quality, i.e. in an uncorrelated manner, in these brain sectors.

The pathological synchronization of neurons manifests in the registration of collective/mass/macro signals in an increased amplitude of the mode, which belongs to the pathological frequency range(s), acquired by means of bandpass filtering or "Empirical Mode Decomposition" (cf. e.g. "The empirical mode decomposition and the Hilbert spectrum for nonlinear and non-stationary time series analysis" by N. E. Huang, Z. Shen, S. R Long, M. C. Wu, H. H. Shih, Q. Zheng, N.-C. Yen, C. C. Tung and H. H. Liu, published in Proc. R. Soc. A: Math. Phys. Eng. Sci. 454, 1998, pages 903 to 995; "Engineering analysis of biological variables: An example of blood pressure over 1 day" by W. Huang, Z. Shen, N. E. Huang and Y. C. Fung, published in Proc. Nat. Acad. Sci. USA 95, 1998, pages 4816 to 4821); the latter is known to the skilled person (cf. e.g. "Pathological synchronization in Parkinson's disease: networks, models and treatments." by C. Hammond, H, Bergman and P. Brown, published in Trends Neurosci, 30, 2007, pages 357 to 364; "Tinnitus Perception and Distress is Related to Abnormal Spontaneous Brain Activity as Measured by Magnetoencephalography" by N. Weisz, S. Moratti, M. Meinzer, K. Dohrmann and T. Elbert, published in PLoS Med 2(6), 2005, pages 546 to 553; "imaging of Thalamocortical Dysrhythmia in Neuropsychiatry" by J. J. Schulman, R. Cancro, S. Lowe, F. Lu, K. D. Walton and R. R. Llinás, published in Front. Hum. Neurosci. 5, 2011, page 69). In this respect, it is, however, not a question of all all-or-nothing principle, i.e. healthy persons can also have power densities in the power spectra in these specific frequency ranges. The determination of the power spectra of such signals, e.g. MEG signals or EEG signals accordingly does not allow any sufficient discrimination between healthy persons and patients (cf. e.g. "Imaging of Thalamocortical Dysrhythmia in Neuropsychiatry by J. J. Schulman, R. Cancro, S. Lowe, F. Lu, K. D. Walton and R. R. Llinás, published in Front. Hum. Neurosci. 5, 2011, page 69). This question can also not be solved by means of standard evoked responses (cf. e.g. "A summation technique for the detection of small evoked potentials." by G. D. Dawson, published in Electroencephalogr. Clin. Neurophysiol, 44, 1954, pages 153 to 154; "Magnetoencephalography: Theory, instrumentation, and applications to non-invasive studies of the working human brain" by M. Hämäläinen, F. Hari, R. J. Ilmoniemi, J. Knuutila and O. V. Lounasmaa, published in Rev. Mod. Phys., Vol. 65, 1993, pages 413 to 497), i.e. cannot be distinguished as power spectra to be evaluated as pathological or non-pathological.

SUMMARY

It is the underlying object of the invention to provide an apparatus and a method which allow a reliable electrophysiologically based diagnosis of a pathological interaction between different brain areas. A distinction should in particular be able to be achieved with the aid of the apparatus and of the method between pathological and non-pathological power spectra in pathological frequency ranges which is measured by electrophysiological signals such as EEG signals, MEG signals or EMG signals. It is in particular the object of the invention to allow a diagnosis of a pathological interaction between the brain areas without requiring a bivariate analysis and measurement of the signals of at least two interacting neural populations for this purpose.

The object underlying the invention is satisfied by the features of the independent claims. Advantageous further developments and aspects of the invention are set forth in the dependent claims.

BRIEF DESCRIPTION OF THE DRAWINGS

The invention will be described in more detail in the following in an exemplary manner with reference to the drawings. There are shown in these.

DETAILED DESCRIPTION

Figure 1:
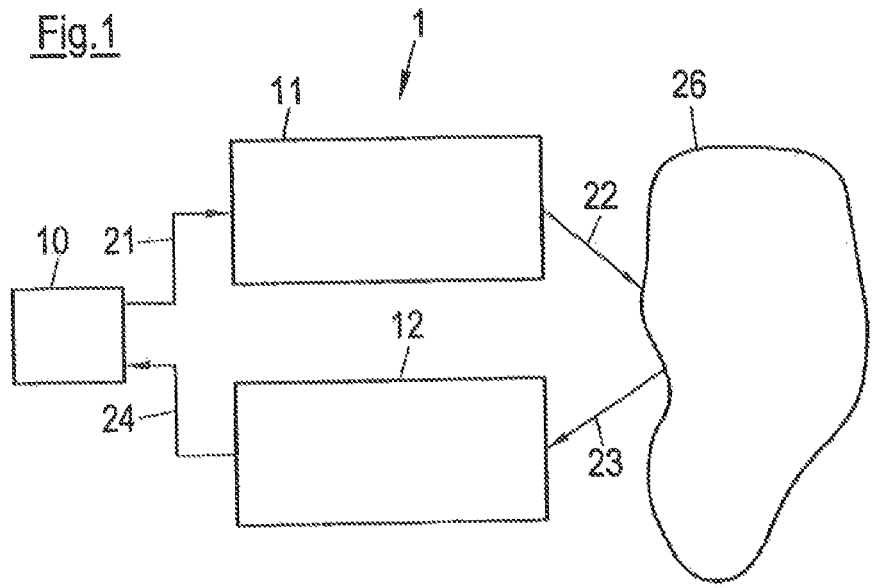
FIG. 1 illustrates a schematic representation of an apparatus for examining a pathological interaction between different brain areas.

An apparatus 1 for examining a pathological interaction between different brain areas is shown schematically in FIG. 1. The apparatus 1 comprises a control and analysis unit 10, a stimulation unit 11 and a measuring unit 12. During the operation of the apparatus 1, the control and analysis unit 10 inter alia carries out a control of the stimulation unit 11. For this purpose, the control and analysis unit 10 generates control signals 21 which are received by the stimulation unit 11. The stimulation unit 11 generates stimuli 22 using the control signals 21 and administers them to a patient. The stimuli 22 are administered to the patient as a sequence of identical individual stimuli and are configured to stimulate the neurons of the patient in the brain areas to be examined.

The stimulation effect achieved by the electrical stimuli 22 is measured with the aid of the measuring unit 12. The measuring unit 12 records one or more measured signals 23 measured at the patient, converts them as required into electrical signals 24 and supplies them to the control and analysis unit 10. The neural activity in the stimulated target sector or in a sector of the brain 26 closely associated with the target sector can in particular be measured using the measuring unit 12.

The control and analysis unit 10 processes the signals 24, e.g. the signals 24 can be amplified and filtered, and analyzes the processed signals 24. In this respect the control and analysis unit 10 examines the distribution of the phases of the measured signals 23 recorded by the measuring unit 12 as a response to the stimuli 22 administered to the patient and determines the probability that the phase distribution differs from an equal distribution. The control and analysis unit 10 determines whether a pathological interaction between the brain areas is present using this analysis. The control and analysis unit 10, for example, can include a processor, e.g. a microcontroller, for carrying out its work.

The stimuli 22 can be stimuli from the group of acoustic, visual, tactile, vibratory, proprioceptive, thermal, olfactory and electrical transcutaneous stimuli. The stimuli 22 can in particular be consciously perceivable by the patient. The stimulus unit 11 and in particular also the control and analysis unit 10 and the measuring unit 12 are non-invasive units in this embodiment, i.e. they are located outside the body of the patient during the operation of the apparatus 1 and are not surgically implanted in the body of the patient.

In an alternative embodiment, the stimulation unit 11 is surgically implanted in the body of the patient and generates electrical stimuli 22 on the basis of the control signals 21 which are administered to the brain and/or to the spinal cord of the patient.

The measuring unit 12 includes one or more sensors which allow the detection of the neural activity of the stimulated neurons with sufficient time resolution. Non-invasive sensors can be used as the sensors, e.g. electroencephalograph (EEG) electrodes, magnetic encephalograph (MEG) sensors and sensors for measuring local field potentials (LFPs). The neural activity can also be determined indirectly by measurement of the accompanying muscle activity by means of electromyograph (EMG) sensors.

Alternatively, the sensors can be implanted in the body of the patient. Epicortical electrodes, deep-brain electrodes, subdural or epidural brain electrodes, subcutaneous EEG electrodes or EMG electrodes and subdural or epidural spinal cord electrodes can serve as invasive sensors, for example. Furthermore, electrodes to be fastened to peripheral nerves can be used as sensors.

Provision can by all means be made that the individual components of the apparatus 1, in particular the control and analysis unit 10, the stimulation unit 11 and/or the measuring unit 12, are separate from one another construction-wise. The apparatus 1 can therefore also be understood as a system.

The apparatus 1 can in particular be used for the diagnosis and treatment of neurological or psychiatric diseases, e.g. Parkinson's disease, essential tremor, tremor resulting from multiple sclerosis as well as other pathological tremors, dystonia, epilepsy, depression, locomotor disorders, cerebellar diseases, obsessive compulsive disorders, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, neuropathic pain, cluster headache, general headache, neuralgia, ataxia, tic disorder or hypertension as well as further diseases which are characterized by pathologically increased neural synchronization.

The above-named diseases can be caused or characterized by a disorder of the bioelectric communication of neural assemblies which are connected in specific circuits. In this respect, a neural population continuously generates pathological neural activity and possibly a pathological connectivity associated therewith (network structure). In this respect, a large number of neurons synchronously form action potentials, i.e. the participating neurons fire excessively synchronously. In addition, there is the fact that the pathological neural population has an oscillatory neural activity, i.e. the neurons fire rhythmically. In the case of neurological or psychiatric diseases, the mean frequency of the pathological rhythmic activity of the affected neural assemblies lies approximately in the range from 1 to 30 Hz, but can also be outside this range. In healthy people, the neurons fire qualitatively differently, however, e.g. in an uncorrelated manner.

Brain areas having a synchronous and oscillatory neural activity moreover interact in a pathologically excessive manner (cf. e.g. "Mapping cortical hubs in tinnitus" by W. Schlee, N. Mueller, T. Hartmann, J. Keil, I. Lorenz and N. Weisz, published in BMC Biol, 7, 2009, page 80).

In accordance with an embodiment, the stimuli 22 administered to the patient in the stimulated neural population effect a reset of the phase of the neural activity of the stimulated neurons. The phase of the stimulated neurons is set to or close to a specific phase value independently of the current phase value by the reset. The phase of the neural activity of the pathological neural population is thus controlled by means of a direct stimulation.

The function of the apparatus 1 will be described in more detail, in the following. The aim in this respect is the detection of diagnosis-relevant, pathologically increased couplings between brain areas in which excessively synchronized, oscillatory neural activity is located.

It has surprisingly been found that simple stimuli as a consequence of the pathologically increased interaction between the brain areas cause complex evoked responses which can be detected by the apparatus 1. I.e. if a stimulus is applied a multiple of times, the associated brain area(s) does or do not always respond with the same stereotypical evoked response with acoustic stimuli, e.g. the primary and secondary auditory cortex. With a sufficiently large ensemble of identical single stimuli 22, e.g. with 50 or 100 individual stimuli 22, two or more families of evoked responses rather occur in one or more time intervals which differ with respect to their mutual phasing. Two families of evoked responses can e.g. be in counter-phase to one another, whereby no significant evoked response results in the standard calculation of an averaged evoked response in comparison with the time interval before the application of the stimulus since the counter-phase evoked responses average out.

Figure 2:
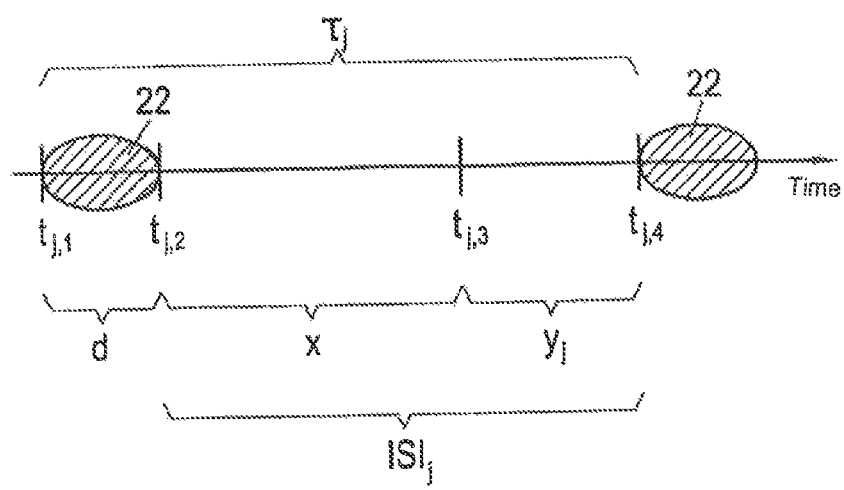
FIG. 2 illustrates a schematic representation of a sequence of identical stimuli for examining the pathological interaction.

FIG. 2 illustrates a stimulus application carried out using the stimulation unit 11 in which N identical individual stimuli 22 are applied, where the number N is, for example, larger than 10 or 50 or 100. The individual stimuli 22 each have a duration d and are applied at times $t_{j,1}$. Here, the index j stands for the jth stimulus 22, where j=1, 2, . . . , N. The index 1 stands for the time of the start of the jth stimulus 22. The jth stimulus 22 end s at the time $t_{j,2}$, where $d=t_{j,2}-t_{j,1}$. The following j+1th stimulus 22 start at the time $t_{j,4}=t_{j+1,1}$, where j=1, 2, . . . , N−1.

The time interval between the end of the jth stimulus 22 and the start of the j+1th stimulus 22 is called, the interstimulus interval $ISI_j$ following the jth stimulus. The interstimulus interval $ISI_j$ can vary from stimulus to stimulus, with it being composed of a fixed portion x and a variable portion $y_j$.

The duration of the total time interval which includes the jth stimulus 22 and the associated interstimulus interval $ISI_j$ amounts to $\tau_j = d+x+y_j$. The fixed portion x of all interstimulus intervals $ISI_j$ should be selected such that earlier evoked responses to the jth stimulus 22 have decayed in every case before the j+1th stimulus 22 is applied. 500 ms≤x≤1000 ms is preferably selected for this reason; however, e.g. to accelerate the examination, smaller values, e.g. down to 300 ms can be selected or, e.g. to detect later more complex evoked responses, larger values, e.g. up to 3000 ms, can also be selected.

The variable portion $y_j$ is preferably selected randomly and with an evenly distributed probability for each interstimulation interval $ISI_j$ from an interval $[0, y_{max}]$. $y_{max}$ is selected in this respect such that it is incommensurable where possible to prevent entrainment effects, that is transient oscillation effects or resonant effects, due to a stimulation whose period matches the period of the pathological oscillatory neural activity. This is important to ensure that only post-effects, so-to-say decay effects, of the individual stimuli 22 can be examined. A sufficiently strongly pronounced entrainment can mask the diagnosis-relevant complex evoked responses. E.g. $y_{max}=\sqrt{2} \cdot 500$ ms can be selected. Other values such as $y_{max}=\sqrt{2} \cdot 1000$ ms or $y_{max}=\sqrt{2} \cdot 300$ ms can also be selected. It is important on the selection of the parameter $y_{max}$ that the mean period $\langle \tau_j \rangle = d+x+y_{max}/2$, where possible differs from the period of the pathological oscillatory neural activity or from whole-number multiples, in particular small whole-number multiples, thereof. Entrainment effects can be avoided in this way.

The measured signals 23 are recorded by the measuring unit 12 simultaneously in time with the application of the individual stimuli 22 and are forwarded to the control and analysis unit 10 in the form of the signals 24. A bandpass filtering can be carried out in the control and analysis unit 10 to filter the frequency bands relevant to the respective disease. These frequency bands are known to the skilled person. With tinnitus patients, pathologically excessive neural oscillatory activity can characteristically be found in low frequency ranges such as in the delta band from 1 to 4 Hz, which can be detected using electroencephalography (EEG) or magnetoencephalography (MEG) (cf. e.g. "Tinnitus Perception and Distress Is Related to Abnormal Spontaneous Brain. Activity as Measured by Magnetoencephalography" by N. Weisz, S. Meinzer, K. Dohrmann and T. Elbert, published in PLoS Med 2(6), 2005, pages 546 to 553).

The signal of the kth mode can be calculated alternatively to a bandpass filtering using the "empirical mode decomposition" method (cf. e.g. "The empirical mode decomposition" and the Hilbert spectrum for nonlinear and non-stationary time series analysis" by N. E. Huang, Z. Shen, S. R. Long, M. C. Wu, H, H. Shih, Q. Zheng, N.-C. Yen, C. C. Tung and H. H. Liu, published in Proc. R. Soc. A: Math. Phys. Eng. Sci. 454, 1998, pages 903 to 995; "Engineering analysis of biological variables: An example of blood pressure over 1 day" by W. Huang, Z. Shen, N. E. Huang and Y. C. Fung, published in Proc. Nat. Acad. Sci. USA 95, 1998, pages 4816 to 4821). The time-dependent signal of the kth mode $s_k(t)$ can e.g. be transformed into the complex plane using the Hilbert transformation and can there be broken down into the associated time-dependent amplitude $A_k(t)$ and the time-dependent phase $\theta_k(t)$, where $s_k(t)=A_k(t)\cos[\theta_k(t)]$, The phases $\theta_k(t)$ are normed in accordance with $$\varphi_k(t) = \frac{\theta_k(t)}{2\pi} \mod 1,$$

where k=1, 2, . . . , M and M indicates the number of modes.

An analysis window [a,b] which generates a time axis is affixed to the start $t_{j,1}$ of each stimulus 22 to analyze the evoked responses recorded by the measuring unit, the time axis being t'∈[a,b], where the start of the associated stimulus 22 in each time window [a,b] lies at t'=0. The maximum permitted width of the window amounts to b−a=d+x since there would otherwise be overlaps of the windows. The prestimulus range and the poststimulus range are symmetrically covered by a=−x/2 and b=d+x/2. The analysis can be preferably focused on the prestimulus range or on the poststimulus range by the selection of a and b. Since the poststimulus dynamics, that is the evoked response after the end of the stimulus, are of primary interest, we will concentrate on them and will select e.g. with a=−x/4 and b=d+3x/4 an asymmetrical window in which the smaller prestimulus range is used for determining the prestimulus measurement base, whereas the long poststimulus range serves for the analysis of the evoked response.

To determine characteristic patterns of the evoked responses of the phases of the kth mode $s_k$, we will look at the distribution of the associated normed phase $\phi_k$ at the times t' relative to the start of stimulus which lies at t'=0. This distribution reads $\{\phi_k(t'+t_{j,1})\}_{j=1, \ldots, N}$, where t'∈[a,b].

Figure 3A:
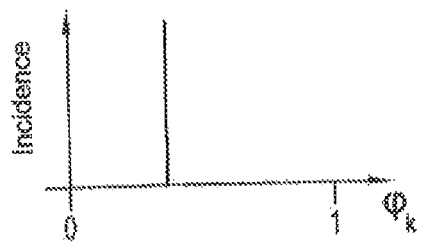
FIGS. 3A to 3D illustrate exemplary representations of possible distributions of the normal phase of a measured signal.

An evoked response of the normed phase $\phi_k$ coupled perfectly in time to the stimulus at the time t', that is a stereotypical evoked response, corresponds to a Dirac distribution at the time t', where $\phi_k$ ideally always adopts the same value at the time t': $\{\phi_k(t'+t_{1,1})\}=\{\phi_k(t'+t_{j,1})\}$ for all j=2, 3, . . . , N. A reinduced ideal phase reset would result in such Dirac distributions such as shown by way of example in FIG. 3A.

Figure 3B:
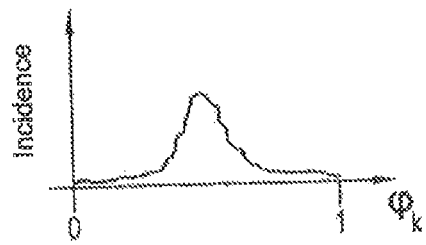

Under realistic conditions, i.e. at biocompatible stimulus intensities and in the presence of noise forces, an accumulation point, a so-called peak, in the distribution $\{\phi_k(t'+t_{j,1})\}_{j=1, \ldots, N}$, is typically found in the case of a reinduced phase reset at a specific part interval after the start of the stimulus. Such a peak is shown by way of example in FIG. 3B.

Figure 3C:
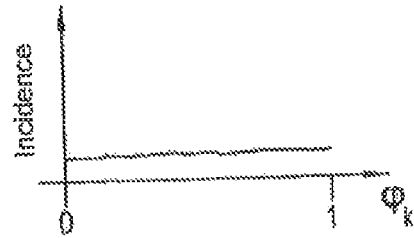

If, in contrast, the stimulus cannot have any effect on the phase dynamics, the distribution $\{\phi_k(t'+t_{j,1})\}_{j=1, \ldots, N}$ is not only equal in the prestimulus range, but also during the stimulus and in the poststimulus range, as is shown by way of example in FIG. 3C.

Figure 3D:
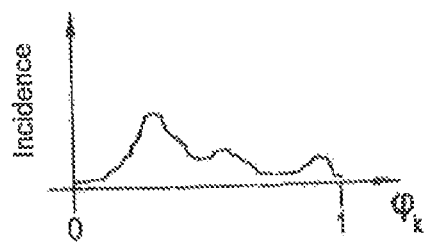

If—e.g. in dependence on the phase at the start of the stimulation—qualitatively different evoked responses of the phase can occur, the distribution $\{\phi_k(t'+t_{j,1})\}_{j=1, \ldots, N}$ has two or more peaks at specific times during the stimulus and/or in the poststimulus range, as FIG. 3D shows by way of example. If it is a question of two peaks of similar width arranged in counter phases, the associated N evoked responses average out if the amplitudes $A_k$ of these two qualitatively different evoked responses do not differ from one another in a relevant manner.

Pathologically excessively coupled neural populations surprisingly characteristically show complex evoked responses of the phase of the associated measured signals such as EEG signals. I.e. epochs occur after the stimulus application in which the distribution $\{\phi_k(t'+t_{j,1})\}_{j=1,\ldots,N}$ significantly differs from an equal distribution. Since the in particular normed phase is a periodic, circular variable, the so-called Kuiper test can be applied which represents the circular variant of the Kolmogorov-Smirnov test (cf. e.g. "Tests concerning random points on a circle" by N. H. Kuiper, published in Proceedings of the Koninklijke Nederlandse Akademie van Wetenschappen, Series A 63, 1960, pages 38 to 47; "Circular Statistics in Biology" by E. Batschelet, Academic Press, London, 1981). The probability $p_k(t)$ with which the distribution $\{\phi_k(t'+t_{j,1})\}_{j=1,\ldots,N}$ differs from an equal distribution at the time t' can be determined with the aid of the Kuiper test. In order finally to determine whether a stimulus effects a significant change of the distribution $\{\phi_k(t'+t_{j,1})\}_{j=1,\ldots,N}$, the prestimulus distributions $\{p_k(t')\}_{t'\in[a,0[}$ are observed from which a threshold value can be calculated. For example, the first percentile and the 99th percentile of the distribution $\{p_k(t')\}_{t'\in[a,0[}$ create a confidence interval where the 99th percentile $\gamma_p$ as the prestimulus measurement base is the decisive value: If $p_k(t')$ exceeds the 99th percentile after a stimulus application, there is a significance deviation from the equal distribution.

The stimuli 22 applied by the stimulation unit 11 can be designed such that they effect a phase reset of the oscillatory neural activity of the stimulated neurons. With primary sensory areas which are stimulated by the associated stimuli, that is e.g. the primary auditory cortex on a stimulation with acoustic stimuli, this phase reset is characteristically early, that is in a close time sequence of the stimulus start or the end of the stimulus (depending on whether it is a question of evoked responses which are triggered by a stimulus start or a stimulus end), e.g. within the first 100 ms. With other, non-sensory brain areas, the phase reset can also occur much later, e.g. after 200 ms. The phase reset primarily mirrors the effect of the stimulus on a brain area. The complex evoked responses detected by the apparatus 1, however, mirror the diagnosis-relevant pathologically increased couplings between brain areas. Time intervals in which a phase reset takes place should therefore be left out of the analysis of the complex evoked responses.

For this purpose, the difference of the phases is determined before and after the application of the stimulus 22. The index of the phase reset belonging to the normed phase $\phi_k$ is determined first using $$\sigma_k(t') = \left| \frac{1}{N} \sum_{j=1}^{N} \exp[i 2\pi \varphi_k(t' + t_{j,1})] \right|.$$

This is the amount of the circular average value of the distribution $\{\phi_k(t'+t_{j,1})\}_{j=1,\ldots,N}$ at the time t'. If the distribution $\{\phi_k(t'+t_{j,1})\}_{j=1,\ldots,N}$ is an equal distribution, i.e. if there is no phase reset, or if it is a Dirac distribution, i.e. a perfect phase reset has taken place, the index of the phase reset is $\phi_k(t')=0$ or $\phi_k(t')=1$.

To determine whether a stimulus effects a significant phase reset, the prestimulus distributions $\{\sigma_k(t')\}_{t'\in[a,0[}$ are observed. For example, the first percentile and the 99th percentile of the distribution $\{\sigma_k(t')\}_{t'\in[a,0[}$ create a confidence interval where the 99th percentile as the prestimulus measurement base is again here also the decisive value: If $\sigma_k(t')$ exceeds the 99th percentile after the application, of the stimulus 22, there is a significant deviation from the equal distribution. It is advantageous as a result of the scaling characteristic of $\sigma_k(t')$, to apply a higher threshold, e.g. fourfold the 99th percentile as the prestimulus measurement base, for the detection of epochs with phase reset. This threshold is termed $\gamma_\sigma$.

A time-dependent mask function $\mu(t')$ can be calculated as follows using the threshold $$\mu(t') = \begin{cases} 0 & \text{for } \sigma_k(t') \geq \gamma_\sigma \\ 1 & \text{for } \sigma_k(t') < \gamma_\sigma \end{cases}$$

The masked probability $P(t')=\mu(t')[p_k(t')-\gamma_p]$, results from this which indicates the probability corrected by the epochs with phase reset and by the prestimulus measurement base with which a complex evoked response, but no phase reset, takes place at the time t'. The masked probability $P(t')$ is determined in the interval $]0,b]$. By definition, a determination in the prestimulus range does not deliver any positive values.

The control and analysis unit 10 can deliver different information. For example, the control and analysis unit 10 can be configured such that it detects at least a time t at which $P(t')>0$ applies to the masked probability. A conclusion can be drawn from this on the presence of an epoch, albeit an only very short epoch, with a complex evoked response which reflects a pathologically increased coupling between brain areas.

Furthermore, the integral masked probability, that is the masked probability integrated over the interval $]0,b]$, can be calculated by the control and analysis unit 10.

In addition, it is sensible to determine the overall duration of the individual epochs with a masked probability above the threshold. The total duration and the characteristic strength, that is the integral masked probability, are the relevant parameters for the pathologically increased coupling between brain areas.

This analysis is carried out for one or more modes of one or more EEG signals, MEG signals or LFP signals or of other measured signals 23 which represent the neural oscillatory activity with sufficient time resolution.

In a possible embodiment, the apparatus 1 has means which allow a visualization of the temporal pattern of the masked probability.

Stimuli 22 will be described in the following which are suitable for an examination of a pathological interaction between different brain areas. It must be noted that the occurrence of the complex evoked responses described in this application depends less on specific information-processing properties of a brain area, but is rather caused by the pathologically high interaction between different brain areas. Accordingly, stimulus parameters and types of stimulus can also be used which differ considerably from the stimulus parameters and types of stimulus described in the following.

In the case of a sensory stimulation, i.e. on the application of in particular vibratory, tactile, proprioceptive, thermal, visual or olfactory stimuli 22, the stimulation parameters are preferably selected such that the stimuli 22 trigger an evoked potential. Stimuli 22 are particularly preferably used which include a plurality of properties or qualities. E.g. visual stimuli 22 can be used which also include edge information and color information in addition to brightness information. Different brain areas or different part regions of brain areas are hereby directly stimulated, whereby the complex evoked responses occur amplified. On an invasive stimulation, i.e. an electrical stimulation of the brain or of the spinal cord of the patient, individual pulses are preferably applied as stimuli 22. Furthermore, low-frequency pulse trains can be applied, with the frequency within the pulse train being e.g. below 50 Hz.

One or more brain areas are directly stimulated by the apparatus in accordance with the invention—depending on the selection of the stimuli. The complex evoked responses which hereby occur are characteristic for a pathologically increased interaction between different brain areas. The apparatus in accordance with the invention can even detect the pathological interaction when only one signal is used which represents the neural activity of only one point of the brain. It is in particular not necessary to measure at least two signals originating from different brain areas and to analyze them with bivariate interaction analyses. The apparatus in accordance with the invention can therefore detect a pathologically increased interaction by means of univariate data analysis.

Individual sounds or frequency mixtures can be multiplied by an envelope, e.g. a Hanning window envelope or a cosine envelope, to generate acoustic stimuli 22. Individual sounds having a length of 100 to 300 ms and a stimulus strength of 15 dB above the auditory threshold and which originate from a purely sinus sound with a Hanning window envelope can be named as an example.

The acoustic stimuli 22 are perceived by the patient via one or both ears, are converted into nerve impulses in the inner ear and are forwarded via the auditory nerve or nerves to neural populations in the brain. The acoustic stimuli 22 are designed such that they stimulate neural populations in the auditory cortex. A specific portion of the auditory cortex is activated on the acoustic stimulation of the inner ear at a specific frequency due to the tonotopic arrangement of the auditory cortex. The tonotopic arrangement of the auditory cortex is described e.g. in the following articles: "Tonotopic organization of the human auditory cortex as detected by BOLD-FMRI" by a Bilecen, K. Scheffler, N. Schmid, K. Tschopp and J. Seelig (published in Hearing Research 126, 1998, pages 19 to 27), "Representation of lateralization and tonotopy in primary versus secondary human auditory cortex" by D. R. M. Langers, W. H. Backes and P. van Dijk (published in NeuroImage 34, 2007, pages 264 to 273) and "Reorganization of auditory cortex in tinnitus" by W. Mühlnickel, T. Elbert, E. Taub and H. Flor (published in Proc. Natl. Acad. Sci. USA 95, 1998, pages 10340 to 10343).

A stimulation with visual stimuli 22 can be based on a variation in luminance or brightness, for example the stimuli 22 can be applied as pulses having varied luminance or brightness. Stimulus checkerboard patterns can be named as examples for use in migraine patients; the stimuli are presented to the patient using a display of the size 22×22 cm with 4×4 black and white checks respectively at a luminance of 0.7 cd/m$^2$ and 117 cd/m$^2$ respectively.

Since different positions in the visual field are imaged at different positions of the retain via the crystalline lens and since the different positions of the retina are in turn connected to different neurons in the brain via the optic nerve, different neural populations can be directly stimulated using optical stimulation elements arranged at different spatial locations. The association of the regions of the visual field with corresponding regions of the brain is described, for example, in the article "Visual Field Maps in Human Cortex" by B. A. Wandell, S. O. Dumoulin and A. A. Brewer, published in Neuron 56, October 2007, pages 366 to 383.

Vibratory, tactile, proprioceptive, thermal, visual or olfactory stimuli 22 can be administered to the patient by means of one or more suitable stimulation units which are placed onto the skin. The stimulation units can include stimulation elements which are led out of a position of rest onto the skin surface of the patient and are possibly pressed into the skin. The stimulation elements can have as corresponding temperature for the application of thermal stimuli. Vibratory, tactile, proprioceptive, visual and olfactory stimuli 22 are in particular suitable for patients with Parkinson's or dystonia. Patients with neuropathic pain can in particular be treated with thermal stimuli in addition to vibratory, tactile, proprioceptive, visual and olfactory stimuli 22.

The direct stimulation of specific regions of the brain by means of vibratory, tactile, proprioceptive, thermal and visual stimuli 22 is made possible by the somatotopic association of regions of the body with these regions. The stimulation units can be attached, for example, to the foot, lower leg and thigh or to the hand, the lower arm and upper arm of the patient. Different neurons are stimulated by the stimuli applied to the respective points due to the somatotopic structure of the neural pathways. The somatotropic association of skin points with regions of the brain is described, for example, in A. Benninghoff et al.: "Lehrbuch der Anatomic des Menschen. [Textbook of Human Anatomy. Presented With Emphasis on Functional Relationships]. 3rd Vol., Nervous System, Skin and Sensory Organs", Urban und Schwarzenberg, Munich 1964. Analog relationships also apply to the olfactory system.

Figure 4:
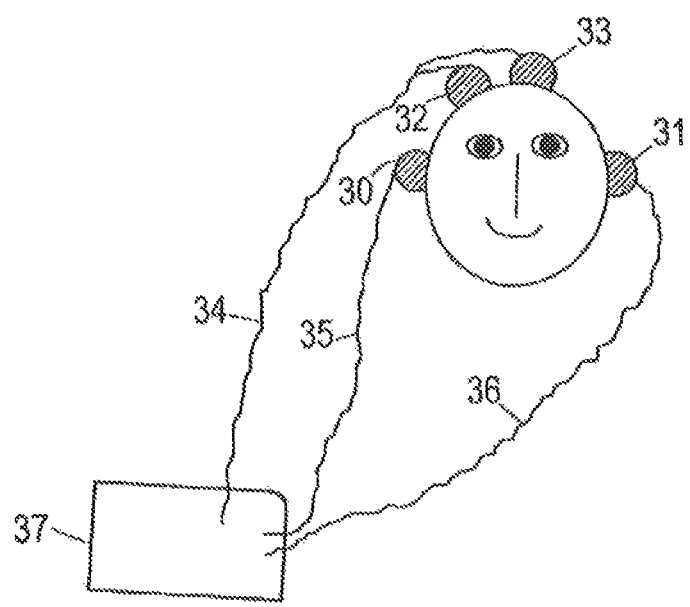
FIG. 4 illustrates a schematic representation of a further apparatus for examining a pathological interaction between different brain areas using acoustic stimuli.

FIG. 4 schematically shows an embodiment of an apparatus for examining a pathological interaction between different brain areas. Acoustic stimuli are administered to the patient via earphones or headphones 30, 31. Non-invasively fixed EEG electrodes 32, 33 as the measuring unit measure the EEG evoked responses. Cables 34, 35, 36 connect the earphones or headphones 30, 31 and the EEG electrodes 32, 33 to a control and analysis unit 37 which has means for calculating the masked probability and, in a possible embodiment, means for visualizing the temporal pattern of the masked probability.

With respect to claim 1, the stimulation unit is in particular configured such that it successively administers identical stimuli to a patient, with the stimuli stimulating neurons of the patient in the brain areas to be examined and each of the successively administered identical stimuli stimulating the same neurons. The measuring unit records measured signals which reproduce a neural activity of the neurons stimulated with the identical stimuli. With an invasive electrical stimulation, the same neutrons can in particular be stimulated in that the electrical stimuli are applied to the same point in the brain or spinal cord of the patient. Tactile, vibratory, proprioceptive, thermal and electrically transcutaneous stimuli stimulate the same neurons when they are applied to the same point of the skin of the patient. Olfactory stimuli stimulate the same neurons when they stimulate the olfactory system at the same point. Visual stimuli which are generated at the same point in the patients visual field likewise stimulate the same neurons. To stimulate the same neurons with acoustic stimuli, the stimuli can have the same frequency or frequencies.

The invention claimed is:

1. An apparatus for examining a pathological interaction between different brain areas, comprising:
a stimulation unit configured to successively administer identical stimuli to a patient, wherein the stimuli stimulate neurons of the patient in the brain areas to be examined;
a measuring unit configured to record measured signals which reproduce a neural activity of the stimulated neurons; and
a control and analysis unit configured to control the stimulation unit and analyze the measured signals, wherein the control and analysis unit is configured such that the control and analysis unit:
controls the stimulation unit to administer the stimuli to the patient; and
transforms the measured signals into a complex plane, examines the distribution of phases of the measured signals recorded by the measuring unit in the complex plane as a response to the stimuli administered to the patient, and determines the probability with which a phase distribution differs from an equal distribution to determine whether a pathological interaction between the different brain areas is present.

2. The apparatus in accordance with claim 1, wherein the measuring unit comprises at least one of EEG electrodes, MEG sensors, EMG sensors, LFP sensors and implantable sensors.

3. The apparatus in accordance with claim 1, wherein the stimulation unit is non-invasive and is configured to generate stimuli from the group consisting of acoustic, visual, tactile, vibratory, proprioceptive, thermal, olfactory and electrical transcutaneous stimuli.

4. The apparatus in accordance with claim 1, wherein the stimulation unit stimulation unit comprises one or more implantable electrodes for administering electrical stimuli.

5. The apparatus in accordance with claim 1, wherein the control and analysis unit controls the stimulation unit to vary intervals between mutually following stimuli.

6. The apparatus in accordance with claim 1, wherein the control and analysis unit is configured to determine a threshold value from the measured signals recorded before the administering of a stimulus and compare the probability determined from the measured signals recorded after the administering of the stimuli with which the phase distribution differs from an equal distribution with the threshold value to determine whether a pathological interaction between the brain areas is present.

7. The apparatus in accordance with claim 1, wherein the control and analysis unit is configured to use a Kuiper test to determine the probability with which the phase distribution differs from an equal distribution.

8. The apparatus in accordance with claim 1, wherein the stimuli administered to the patient by the stimulation unit effect a phase reset of a pathologically synchronous and oscillatory activity of the stimulated neurons.

9. The apparatus in accordance with claim 8, wherein, on the determination of the probability with which the phase distribution differs from an equal distribution, the measured signals in the time periods in which a phase reset of the pathologically synchronous and oscillatory activity of the stimulated neurons takes place remain out of consideration.

10. The apparatus in accordance with claim 1, wherein the control and analysis unit is further configured to detect at least one point in time at which the probability with which the phase distribution differs from an equal distribution is above a predefined threshold value.

11. The apparatus in accordance with claim 1, wherein the control and analysis unit is further configured to integrate the probability with which the phase distribution differs from an equal distribution over a predefined time period.

12. The apparatus in accordance with claim 1, wherein the control and analysis unit is further configured to determine the total duration of time periods in which the probability with which the phase distribution differs from an equal distribution is above a predefined threshold value.

13. A method of examining a pathological interaction between different brain areas, the method comprising:
successively administering identical stimuli to a patient, wherein the stimuli stimulate neurons of the patient in the brain areas to be examined;
recording measured signals that reproduce a neural activity of the stimulated neurons; and
transforming the measured signals into a complex plane by examining a distribution of phases of the measured signals recorded in the complex plane as a response to the stimuli administered to the patient and determining a probability with which a phase distribution differs from an even distribution to determine whether a pathological interaction between the different brain areas is present.

14. The method in accordance with claim 13, further comprising:
determining a threshold value from the measured signals recorded before the administering of a stimulus; and
comparing the probability determined from the measured signals recorded after the administering of the stimuli with which the phase distribution differs from an equal distribution with the threshold value to determine whether a pathological interaction between the brain areas is present.

15. The method in accordance with claim 13, further comprising using a Kuiper test to determine the probability with which the phase distribution differs from an equal distribution.

16. The method in accordance with claim 13, wherein the stimuli administered to the patient effect a phase reset of a pathologically synchronous and oscillatory activity of the stimulated neurons.

17. The method in accordance with claim 16, wherein, on the determination of the probability with which the phase distribution differs from an equal distribution, the measured signals in the time periods in which a phase reset of the pathologically synchronous and oscillatory activity of the stimulated neurons takes place remain out of consideration.

18. The method in accordance with claim 13, further comprising successively administering the identical stimuli to the patient at the different brain areas using at least one of tactile, vibratory, proprioceptive, thermal and electrically transcutaneous stimuli, such that each of the identical stimuli stimulates a same plurality of neurons, respectively, each time the respective stimuli is applied to a same point of the skin of the patient.

19. The method in accordance with claim 13, further comprising successively administering the identical stimuli to the patient at the different brain areas using olfactory stimuli, such that each of the identical stimuli stimulates a same plurality of neurons, respectively, each time the respective stimuli stimulates a same point of the olfactory system of the patient.

20. The method in accordance with claim 13, further comprising successively administering the identical stimuli to the patient at the different brain areas using visual stimuli, such that each of the identical stimuli stimulates a same plurality of neurons, respectively, each time the respective stimuli stimulates a same point in a visual field of the patient.

21. The method in accordance with claim 13, further comprising successively administering the identical stimuli to the patient at the different brain areas using tactile stimuli, such that each of the identical stimuli stimulates a same plurality of neurons, respectively, each time the respective stimuli stimulates has a same frequency or frequencies when it is administered to the patient.

22. The method in accordance with claim 13, further comprising successively administering the identical stimuli to the patient at the different brain areas using invasive electrical stimuli, such that each of the identical stimuli stimulates a same plurality of neurons, respectively, each time the respective stimuli stimulates a same point in the brain or spinal cord of the patient.

* * * * *